United States Patent
Shitara et al.

(10) Patent No.: US 8,295,000 B2
(45) Date of Patent: Oct. 23, 2012

(54) METHOD AND ITS APPARATUS FOR INSPECTING A MAGNETIC DISK

(75) Inventors: Kenichi Shitara, Kamisato (JP); Ayumu Ishihara, Kamisato (JP)

(73) Assignee: Hitachi High-Technologies Corporation, Tokyo (JP)

( * ) Notice: Subject to any disclaimer, the term of this patent is extended or adjusted under 35 U.S.C. 154(b) by 93 days.

(21) Appl. No.: 13/012,883

(22) Filed: Jan. 25, 2011

(65) Prior Publication Data

US 2011/0188143 A1    Aug. 4, 2011

(30) Foreign Application Priority Data

Jan. 29, 2010    (JP) .................................. 2010-017787

(51) Int. Cl.
*G11B 27/36* (2006.01)
(52) U.S. Cl. ......................................................... 360/31
(58) Field of Classification Search ................... 360/31, 360/53, 55, 69, 72.1, 77.12, 135; 369/13.15, 369/13.17; 382/141; 359/557
See application file for complete search history.

(56) References Cited

U.S. PATENT DOCUMENTS

| | | | | |
|---|---|---|---|---|
| 5,067,039 A | * | 11/1991 | Godwin et al. | 360/135 |
| 5,247,493 A | * | 9/1993 | Kime et al. | 369/13.17 |
| 5,305,294 A | * | 4/1994 | Kime et al. | 369/13.17 |
| 6,057,962 A | | 5/2000 | Hirunuma et al. | |
| 6,178,142 B1 | * | 1/2001 | Fujita | 369/13.15 |
| 6,721,123 B2 | * | 4/2004 | Sueki et al. | 360/77.12 |
| 6,731,574 B1 | * | 5/2004 | Abe et al. | 369/44.32 |
| 6,856,484 B2 | * | 2/2005 | Johnson et al. | 360/77.12 |
| 7,149,338 B2 | * | 12/2006 | Takai et al. | 382/141 |
| 7,463,762 B2 | * | 12/2008 | Takai et al. | 382/141 |
| 2003/0142592 A1 | * | 7/2003 | Mitani et al. | 369/13.14 |

FOREIGN PATENT DOCUMENTS

JP    11-86282 A    3/1999

* cited by examiner

*Primary Examiner* — Fred Tzeng
(74) *Attorney, Agent, or Firm* — Mattingly & Malur, PC

(57) ABSTRACT

In order to implement efficient read/write testing by firstly determining read/write test area-sampling positions based on position information relating to any defects detected during optical inspection, and then conducting read/write tests only upon areas neighboring the defects detected during the optical inspection, a magnetic disk to be inspected is retained on a spindle and moved under this state between an optical type of inspection apparatus and a read/write test apparatus, in which apparatus configuration the read/write test apparatus uses position information on any defects detected by the optical type of inspection apparatus and conducts read/write tests only upon neighboring areas of the defects detected by the optical type of inspection apparatus.

16 Claims, 12 Drawing Sheets

ENLARGED CROSS-SECTIONAL VIEW OF DEFECTIVE PORTION

METHOD AND ITS APPARATUS FOR INSPECTING A MAGNETIC DISK

BACKGROUND

The present invention relates generally to apparatuses for inspecting magnetic disks. More particularly, the invention concerns an inspection method and apparatus suitable for detecting magnetic-disk surface defects in magnetic recording characteristics as well as in appearance.

Magnetic disks (storage media) are becoming enhanced in recording density each year, and this tendency is making it necessary to dimensionally manage smaller disk-surface defects during manufacturing processes. At the same time, the increase in recording density is calling for the suppression of an increase in the time required for the read/write tests conducted to inspect recording states by writing data onto magnetic disks and reading out the data.

A technique for responding to such needs is disclosed in JP-A-11-86282 (Patent Document 1). JP-A-11-86282 describes a read/write test method including: first, inspecting magnetic disks optically with an optical inspection apparatus and detecting defects thereof; next dividing the inspected magnetic disks into groups based on detected defect data; and activating a certification test apparatus to write data, with a magnetic head, only onto any magnetic disks that have been determined to be of the group requiring electrical characteristics inspection, then read out the written data from each magnetic disk, and inspect a recording state of the magnetic disk.

Another related technique is disclosed in U.S. Pat. No. 6,057,962 (Patent Document 2). U.S. Pat. No. 6,057,962 describes a read/write test method that including: first, inspecting the surfaces of magnetic disks optically with an optical inspection apparatus and removing any magnetic disks found to have particles sticking to the disk surface; next after sampling some of the non-removed magnetic disks, activating an apparatus to write data onto each sampled magnetic disk using a magnetic head, then read out the written data, and inspect a recording state of the magnetic disk.

As the recording densities of magnetic disks (storage media) are enhanced, the flying heights of magnetic heads during the rotation of the magnetic disks are coming to decrease, and even magnetic disks with smaller particles or projections or depressions on the surface thereof may be determined to be defective, during read/write tests. This indicates that even the magnetic disks whose surfaces have been optically inspected with an optical inspection apparatus and determined to be non-defective may have, on the surface, such small particles or projections or depressions that cause the disk to be recognized as a defective one during read/write tests.

Accordingly, as described in Patent Document 1, even if disk surface defect optical inspections with an optical inspection apparatus indicate the presence of no defective magnetic disks, some of these disks may require electrical characteristics inspection, or read/write tests, according to a particular surface state.

In the magnetic disk inspection methods described in Patent Documents 1 and 2, data on the defects that were detected during optical inspection of magnetic disk surfaces with an optical inspection apparatus has not been utilized during read/write tests. Since read/write tests require a greater deal of inspection time than that for optical inspection, it is absolutely necessary that several sampled areas on the magnetic disk be inspected on a mass-production line basis. In the above conventional methods, however, since optical inspection result information has not been used during sampling-position selection for the read/write tests, inspection has only been possible by sampling predetermined positions on the magnetic disk independently of the defect positions.

SUMMARY

The present invention enables efficient read/write testing by selecting read/write test area-sampling positions from position information on defects detected during optical inspection, and then conducting the read/write tests only upon areas neighboring the detected defects. This further enhances reliability of read/write test results.

That is, in an aspect of the present invention, a magnetic disk to be inspected is retained on a spindle and moved under this state between an optical type of inspection apparatus and a read/write test apparatus. This enables the read/write test apparatus to use position information on any defects detected by the optical type of inspection apparatus, and the read/write test apparatus to conduct inspections only upon areas neighboring the detected defects. Thus, efficient read/write testing is achieved and inspection throughput improves.

In addition, the apparatus that inspects defects on a surface of the magnetic disk which is a sample includes: optical inspection means for optically inspecting the surface of the sample and detecting defects on the surface of the sample; read/write test means for determining a state of the sample by conducting read/write tests during which the read/write test means itself uses magnetic heads to write information onto the sample inspected by the optical inspection means and read the written information from the sample; and spindle shaft means for rotating the sample rested and retained thereupon, the spindle shaft means, upon completion of the inspection by the optical inspection means, moving the rested sample to the read/write test means for execution of the read/write tests.

Furthermore, the apparatus that inspects defects on surfaces of both sides of the magnetic disk which is a sample includes: double-surface simultaneous optical inspection unit which optically inspects surfaces of both sides of the sample at the same time and detecting defects on the surfaces of both sides of the sample; read/write test unit which determines a state of defects detected by the optical inspection unit, by conducting read/write tests during which the read/write test unit itself uses magnetic heads to write information onto positions inclusive of the detected defects on the surfaces of both sides of the sample, and read the written information from the sample; and spindle shaft unit which is constructed to move, with the sample rested and retained thereon, between the double-surface simultaneous optical inspection means and the read/write test means, the spindle shaft unit rotationally driving the rested sample at a position of the double-surface simultaneous optical inspection means and that of the read/write test means.

In a further aspect of the present invention, a method for inspecting a magnetic disk includes: optically inspecting surfaces of both sides of the magnetic disk at the same time and detecting defects on the surfaces of both sides of the sample; and conducting read/write tests to write information onto positions inclusive of any defects detected on either of the surfaces of both sides of the sample by the optical inspecting and read the written information to determine a state of the detected defects on the sample; wherein in the optically inspecting step, the surfaces of both sides of the sample are inspected at the same time while the sample is in a rested and retained condition on a spindle shaft which is constructed to rotationally drive the sample rested and retained thereon.

In a further aspect of the present invention, the method for inspecting a magnetic disk includes: optically inspecting surfaces of both sides of the magnetic disk retained as a sample on a rotatably constructed spindle shaft at the same time, and detecting defects on the surfaces of both sides of the sample; moving the sample from the optical inspection station to a read/write test station with the sample remaining retained on the spindle shaft; and conducting read/write tests by using magnetic heads to write information onto positions inclusive of the defects detected on either of the surfaces of both sides of the sample detected by the optical inspection and read the written information, whereby a state of the detected defects on the sample is determined by the read/write test.

According to the present invention, since position information on the defect candidates detected by the optical type of inspection apparatus is used for the read/write test apparatus to inspect only peripheral areas of the positions of the defect candidates, the read/write tests are conducted efficiently and reliability of read/write test results is enhanced.

In addition, the optical type of inspection apparatus and the read/write test apparatus are integrated to construct a compact inspection apparatus in its entirety.

These features and advantages of the invention will be apparent from the following more particular description of preferred embodiments of the invention, as illustrated in the accompanying drawings.

BRIEF DESCRIPTION OF THE DRAWINGS

FIG. 10A is a diagram of a readout signal waveform of an area including the concave-like defect during read/write tests in the first embodiment;

FIG. 10B is schematically representing a position and cross-sectional shape of the defect on the sample;

FIG. 11A is a diagram of a readout signal waveform of an area including the convex-like defect during read/write tests in the first embodiment;

FIG. 11B is schematically representing a position and cross-sectional shape of the defect on the sample;

DESCRIPTION OF THE PREFERRED EMBODIMENTS

In the present invention, a magnetic disk to be inspected is retained on a spindle and moved under this state between an optical type of inspection apparatus and a read/write test apparatus. This enables the read/write test apparatus to use position information on any defects detected by the optical type of inspection apparatus, and the read/write test apparatus to test only areas neighboring the detected defects. Thus, efficient read/write testing is achieved and inspection throughput improves.

Hereunder, more specific examples of the above will be described using the accompanying drawings.

First Embodiment

A system configuration for inspecting both upper and lower surfaces of a magnetic disk at the same time is described below as a first embodiment.

Figure 1:
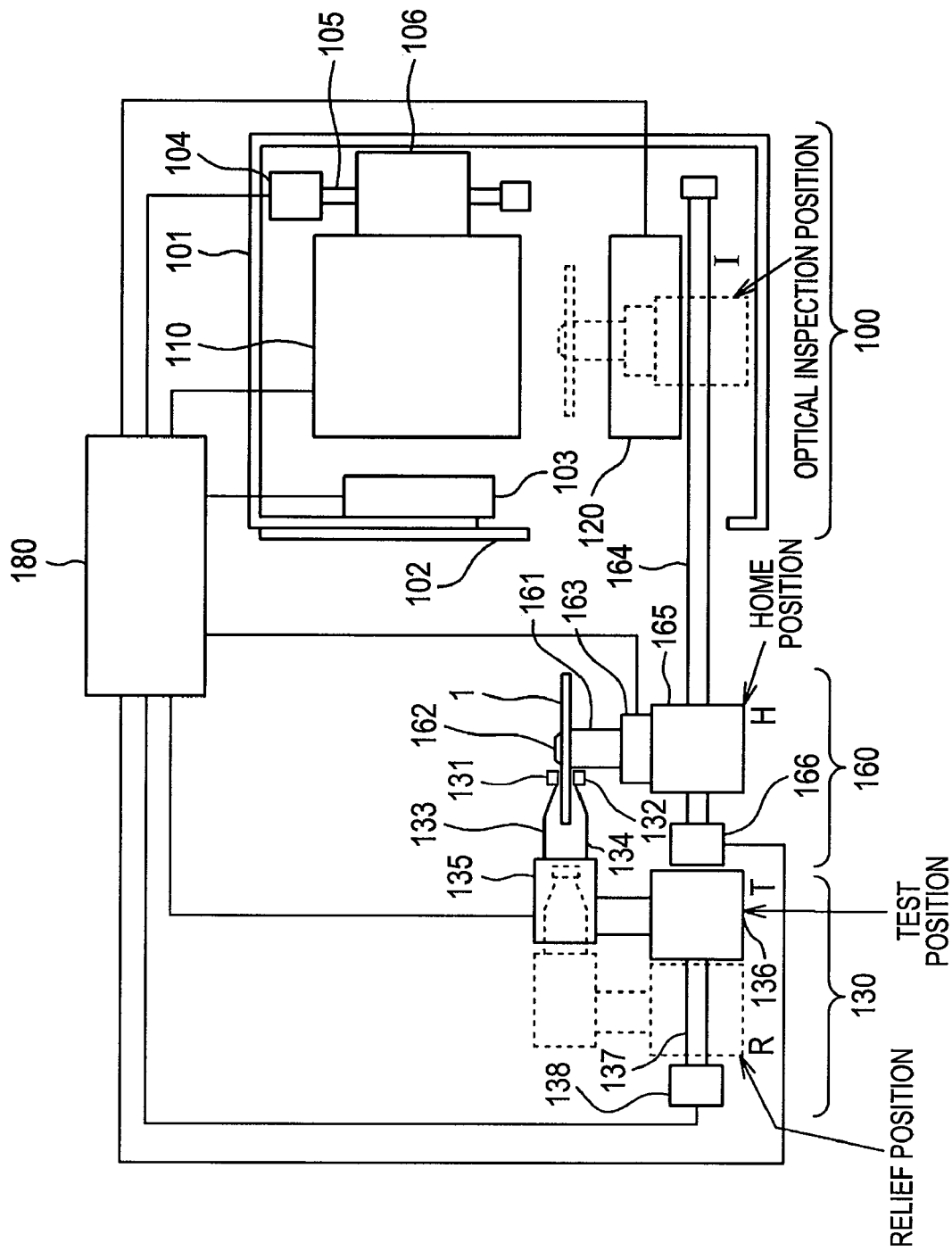
FIG. 1 is a block diagram showing a total system configuration of an inspection apparatus according to a first embodiment.

FIG. 1 is a block diagram showing a total system configuration of the inspection apparatus according to the present embodiment, wherein the apparatus includes an optical inspection apparatus and a read/write test apparatus in integrated form.

More specifically, the entire apparatus includes an optical inspection unit 100, a read/write test unit 130, a sample transport unit 160, and a signal-processing and total control unit 180.

The optical inspection unit 100 includes an upper-surface inspection unit 110 and a lower-surface inspection unit 120, is totally shrouded with a protective cover 101, and uses a shutter 102 to open and close a section that loads and unloads a sample (magnetic disk) 1. The upper-surface inspection unit 110 is fixed to a block 106 driven by a driving motor 104 to move vertically along a guide shaft 105 so that the inspection unit can be moved away to a retreat position during the loading/unloading of the sample 1. The upper-surface inspection unit 110 also uses a laser displacement gauge 103 to detect height of the sample surface during the inspection.

The read/write test unit 130 includes: one pair of magnetic heads, 131 and 132, for inspecting the upper and lower surfaces of the sample 1 at the same time; one pair of gimbals, 133 and 134, for supporting the paired magnetic heads 131, 132; a fixing block 135 for fixing the paired gimbals 133, 134; a support block 136 for supporting the fixing block 135 and loading/unloading the paired magnetic heads 131, 132 towards/from the sample 1; a first guide shaft 137 for guiding the support block 136; and a first motor 138 for moving the support block 136 along the guide shaft 137.

The sample transport unit 160 includes: a rotatable spindle shaft 161 for holding the sample 1; a chuck 162 for clamping the sample 1; a spindle motor 163 for rotationally driving the spindle shaft 161; a moving stage 165 for holding the spindle motor 163 and movable along a second guide shaft 164; and a second motor 166 for moving the moving stage 165 along the guide shaft 164.

The signal-processing and total control unit 180 receives detection signals from the optical inspection unit 100 and the paired magnetic heads 131 and 132 of the read/write test unit 130, and processes the detection signals. In addition, the signal-processing and total control unit 180 receives a sample surface height detection signal from the laser displacement gauge 103, and controls height of the upper-surface inspection unit 110 by controlling the driving motor 104. Furthermore, the control unit 180 controls and drives the shutter drive 102, the driving motor 104, the first motor 138, the spindle motor 163, and the second motor 166.

Next, a sequence for inspecting the sample 1 using the inspection apparatus of FIG. 1 is described below by referring to FIGS. 2 to 5.

Figure 2:
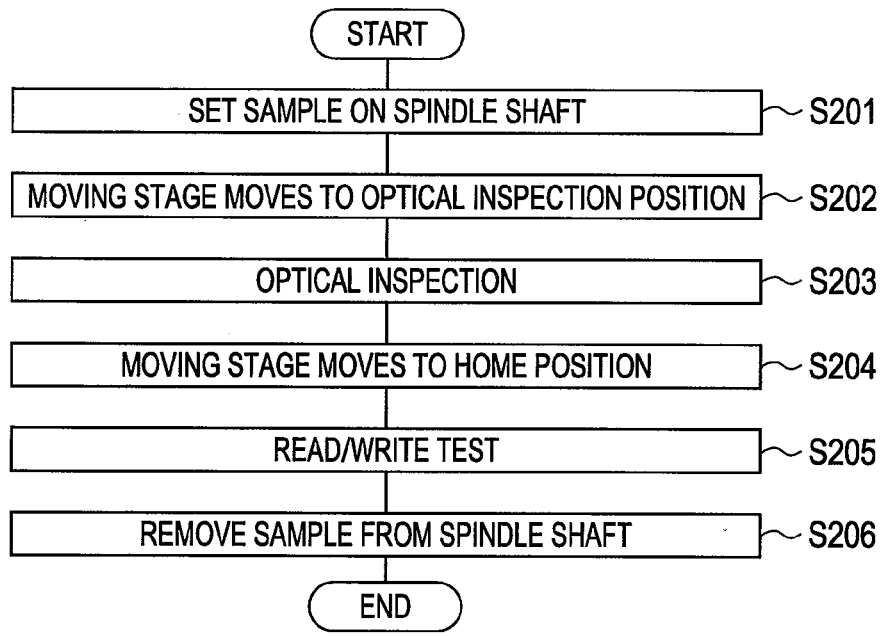
FIG. 2 is a flow diagram showing a flow of processing in the inspection apparatus according to the first embodiment.

A total process flow is first described below using the flowchart shown in FIG. 2.

In step S201, the sample 1 is set on the spindle shaft 161 by a handling robot (not shown), with the moving stage 165 at its home position H, and the sample 1 is retained by clamping with the chuck 162. In step S202, the moving stage 165 is driven by the second motor 166 to move along the second guide shaft 164 to the position of the optical inspection unit 100 and then stops at an optical inspection position I. In step S203, both side surfaces of the sample 1 are optically inspected at the optical inspection position I by the upper-surface inspection unit 110 and the lower-surface inspection unit 120, and inspection signals from the inspection units 110 and 120 are transferred to and processed by the signal-processing and total control unit 180 to detect defects on the sample 1.

After the optical inspections completes, in step S204, the moving stage 165 is driven by the second motor 166 to move along the second guide shaft 164 and reaches to the home position H. In step S205, the read/write test unit 130 conducts read/write tests upon both the upper and lower surfaces of the sample 1 at the same time at the home position H using the paired magnetic heads 131 and 132 controlled by the total control unit 180, detection signals from the magnetic heads 131 and 132 are transferred to the signal-processing and total control unit 180 for processing. Upon completion of the read/write tests, the chuck 162 unclamps the sample 1, whereby the sample 1 is removed from the spindle shaft 161 by the handling robot (not shown) to complete the successive inspection steps.

Figure 3A:
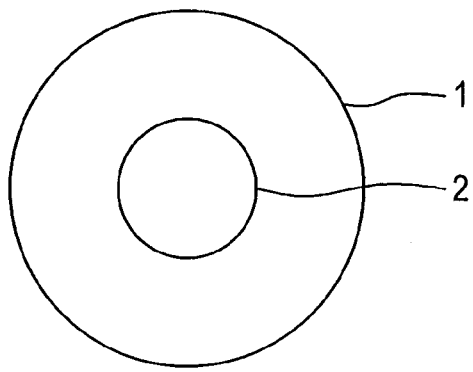
FIG. 3A is a plan view of a sample (magnetic disk)
Figure 3B:
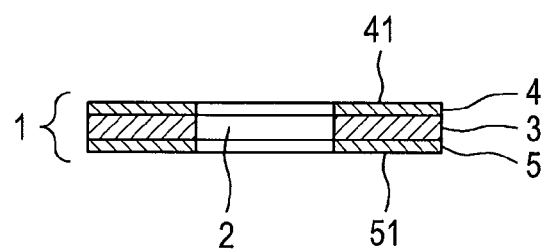
FIG. 3B is a sectional view of a sample (magnetic disk)

As shown in FIG. 3A, the magnetic disk that is the sample 1 has a doughnut shape with a hole 2 in a central section. As shown in FIG. 3B, the magnetic disk is also of a multilayered cross-sectional structure with thin film layers 4 on one surface and the other thin film layers 5 on another surface of a glass substrate 3.

Figure 4:
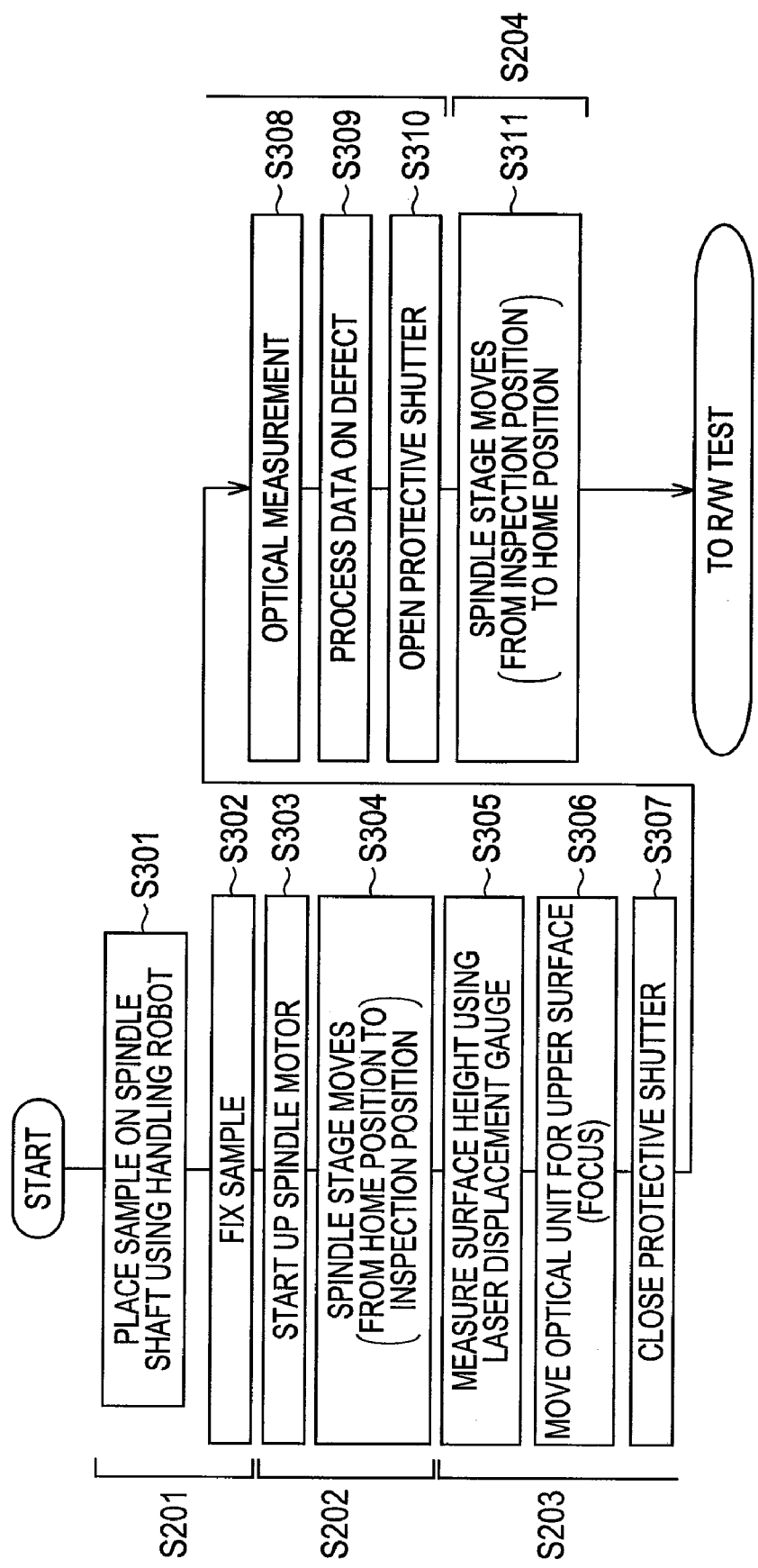
FIG. 4 is a flow diagram for describing optical inspection process steps according to the first embodiment.

Operation from steps S201 to S204, inclusive of optical inspection step S203, is described in detail below using FIG. 4.

First, while the moving stage 165 is at the home position H, the magnetic disk (storage medium) that is the sample 1 to be inspected is placed on the spindle 161 by the handling robot (not shown) so that the hole 2 in a central section of the disk fits onto the chuck 162 of the spindle 161 (step S301: corresponding to step S201).

Next, the chuck 162 clamps the sample 1 at an inner circumferential portion of the hole 2 to fix the sample 1 to the spindle 161 (step S302).

The second motor 166 is then activated (step S303), whereby the moving stage 165 moves from the home position H to the optical inspection position I along the second guide shaft 164 (step S304). At this time, the shutter 102 of the optical inspection unit 100 is open.

Optical inspection step S203 is started upon an arrival of the moving stage 165 at the optical inspection position I.

First, a command from the signal-processing and total control unit 180 operates the spindle motor 163 to rotate the sample 1 and makes the laser displacement gauge 103 measure the surface height of the rotating sample 1 (step S305). Another command from the signal-processing and total control unit 180 operates the driving motor 104 to move the block 106 vertically along the guide shaft 105. Thus, a vertical position of the upper-surface inspection unit 110 fixed to the block 106 is controlled for the upper-surface inspection unit 110 to match a focal position of its optical system to the surface of the sample 1 (step S306).

During the above surface-height measurement of the sample 1 and focal-position matching of the optical system of the upper-surface inspection unit 110, the shutter 102 of the optical inspection unit 100 is closed to prevent external light to enter into the protective cover 101 (step S307).

After the above focal-position matching operation and the closing of the shutter 102, the spindle motor 163 is driven to rotate the sample 1, and the second motor 166 is driven to move the moving stage 165 at a constant speed along the second guide shaft 164 while the sample 1 is rotating, and during the movement of the moving stage 165, the upper-surface inspection unit 110 and the lower-surface inspection unit 120 optically inspect the upper and lower surfaces, respectively, of the sample 1 and detect light from defect candidates on the sample (step S308).

Detection signal of defect candidates that the upper-surface inspection unit 110 or the lower-surface inspection unit 120 has detected is sent to and processed by the signal-processing and total control unit 180, where the detection signal waveform data and position information relating to the defect candidates are then extracted from the processed data (step S309).

When the moving stage 165 reaches a predetermined position along the second guide shaft 164, the inspection is completed and the second motor 166 is stopped to drive. After that, the shutter 102 is opened (step S310) and then optical inspection step S203 is finished.

Next, the second motor 166 drives the moving stage 165 to move it from the optical inspection position I to the home position H along the second guide shaft 164 (step S311).

A process flow of the read/write tests at the home position H is next described below by referring to FIG. 5.

First, when the moving stage 165 is back at its home position H, a command from the signal-processing and total control unit 180 activates the spindle motor 163 to turn the sample 1 at a predetermined rotational speed for the read/write tests (step S401). Next, another command from the signal-processing and total control unit 180 activates the first motor 138 to move the support block 136 from the retreat position R to a test position T along the guide shaft 137. Thus, the read/write test heads 131 and 132 at front ends of the gimbals 133 and 134 supported by the fixing block 135 are set at an inspection-starting position on the sample 1 turning at the predetermined rotating speed for the read/write tests (step S402).

Next, the support block 136 that has been driven by the first motor 138 moves to a first one of certification test areas in a radial direction on the sample 1 (step S403). At this time, based on the position data relating to the upper- and lower-surface defect candidates on the sample 1, which was obtained during optical inspection step S203, the certification test areas are already determined in the signal-processing and total control unit 180.

Next at this inspection position, under the control of the signal-processing and total control unit 180, write head that is part of the read/write heads 131 and 132 writes data at a predetermined frequency onto the magnetic disk that is the sample 1 (step S404). After this, a read head that is another part of the read/write heads 131 and 132 reads out the data from the position on the sample 1 where the write head has written the data (step S405). The data that the read head has thus read is sent to the signal-processing and total control unit 180, where the read data then undergoes processing and the certification test is executed (step S406).

Next after the certification test in the first radial area, the first motor 138 drives the support block 136 to position the read/write heads 131, 132 in a second radial area, where similar certification test steps from S403 to S406 are then executed. In this manner, steps S403 to S406 are repeatedly executed until the certification test has been completed for all selected areas (step S407).

Completion of the certification test is followed by step S408 beginning with error checking. In step S408, if an error is detected in the certification test, firstly the first motor 138 drives the support block 136 to position the read/write heads 131 and 132 at an area where the error was detected. Next, a retest based on a command from the signal-processing and total control unit 180 is conducted under retrial conditions. The retest includes: writing data onto the sample 1 using the write head of the read/write heads 131, 132; and reading out the written data from the sample 1 using the read head of the read/write heads 131, 132.

Next, the error is determined from results of the retest, and the error information is stored into the signal-processing and total control unit 180 (step S409).

Upon retest step S408 being completed for all errors detected in step S406 and related error information being stored into the signal-processing and total control unit 180, the first motor 138, under a command from the control unit 180, drives the support block 136 to return it to the retreat position R, so that the read/write heads 131, 132 go back from the sample 1 (step S410).

Next, the spindle motor 163 stops rotating (step S411), the chuck 162 unclamps the sample 1 (step S412), and the handling robot (not shown) removes the sample 1 from the spindle 161 (step S413) to complete the read/write tests.

Detailed configurations of the upper-surface inspection unit 110 and lower-surface inspection unit 120 of the optical inspection unit 100 used in optical inspection step S203 are described below using FIGS. 6 to 8B. Flows of related inspection process steps are also described below.

Figure 6:
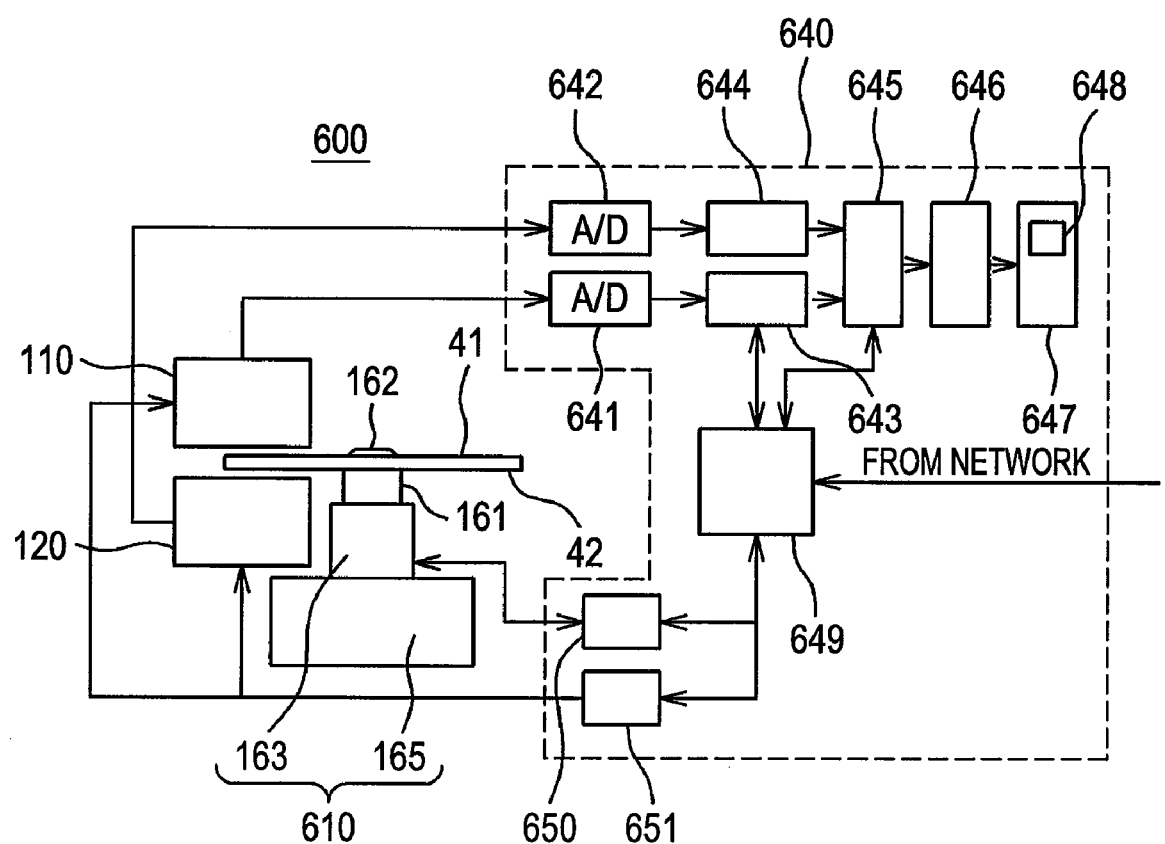
FIG. 6 is a block diagram showing an overall configuration of an optical inspection apparatus in the first embodiment.

FIG. 6 is a block diagram showing an overall configuration of a double-surface defect detection unit 600 for detecting defects on the upper and lower surfaces of the magnetic disk, the defect detection unit 600 being inclusive of the upper-surface inspection unit 110 and lower-surface inspection unit 120 of the optical inspection unit 100. Major constituent elements of the double-surface defect detection unit 600 are: a table unit 610 on which a sample to be inspected is held, an optical system 620 for upper-surface inspection, an optical system 630 for lower-surface inspection, and a signal-processing and control system 640.

The table unit 610 includes a rotatable spindle 161 on which the sample (magnetic disk) 1 is held, a spindle motor 163, and a moving stage 165. The moving stage 165, as is described in FIG. 1, is constructed to be movable along a second guide shaft 164 when driven by a second motor 166.

The signal-processing system 640 in FIG. 6 includes: a first A/D conversion unit 641 that converts an analog detection signal from the upper-surface inspection optical system 620 into digital form; a second A/D conversion unit 642 that converts an analog detection signal from the lower-surface inspection optical system 630 into digital form; a first signal-processing unit 643 that processes a signal output from the first A/D conversion unit 641; a second signal-processing unit 644 that processes a signal output from the second A/D conversion unit 642; an integrated signal-processing unit 645 that integrates and processes the signals processed by the first signal-processing unit 643 and the second signal-processing unit 644; a storage unit 646 that stores a result of processing by the integrated signal-processing unit 645; an input/output unit 647 that includes a display screen 648 for displaying the result of processing by the integrated signal-processing unit 645, and for entering inspection parameters; an optical inspection apparatus control unit 649 that controls the entire optical inspection apparatus; a table control unit 650 that, upon receiving a control signal from the optical inspection apparatus control unit 649, controls the table unit 610 at an optical inspection position; and an inspection optical system control unit 651 that, upon receiving control signals from the optical inspection apparatus control unit 649, controls the upper-surface inspection optical system 620 and the lower-surface inspection optical system 630.

The signal-processing and control system 640 in FIG. 6 is included in the signal-processing and total control unit 180 of the total inspection apparatus configuration shown in FIG. 1.

Figure 7:
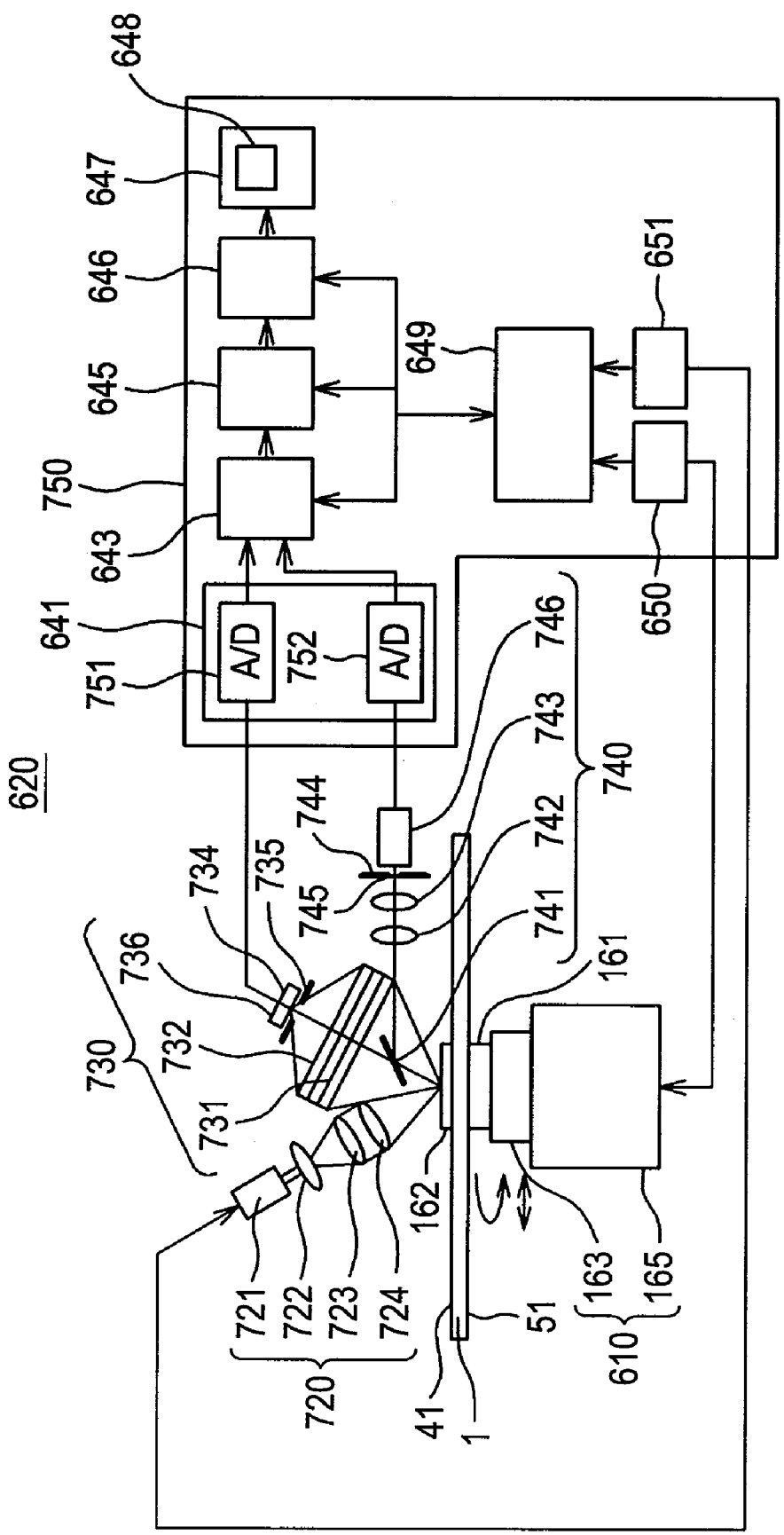
FIG. 7 is a block diagram showing a configuration of an optical system for upper-surface inspection in the first embodiment.

FIG. 7 is a block diagram showing a detailed configuration of the upper-surface inspection optical system 620. Major constituent elements of the upper-surface inspection optical system 620 are an optical system 720 for illumination light, an optical system 730 for detecting scattered light, an optical system 740 for detecting specularly reflected light, and a signal-processing and control system 750 (included in the signal-processing and control system 640 shown in FIG. 6).

The illumination light optical system 720 includes: a laser light source 721, a magnifying lens 722 for expanding a laser emitted from the laser light source 721 in beam diameter, a converging lens 723 for converging the laser expanded in beam diameter, and a focusing lens 724 for focusing the converged laser upon the upper surface 41 of the sample 1.

The scattered-light detection optical system 730 includes: a first aspherical Fresnel lens 731 equivalent to an objective lens, for converging only scattered light of all light reflected (specularly reflected light and scattered light) from the upper surface 41 of the sample 1; a second aspherical Fresnel lens 732 equivalent to a focusing lens, for focusing the scattered light that has been converged; a pinhole plate 735 having a pinhole 734 to let the scattered light pass through upon being focused by the second aspherical Fresnel lens 732, the pinhole plate 735 serving to block stray light other than the scattered light; and a first photoelectric converter 736, for example an avalanche photodiode (APD) or photomultiplier tube (PMT), for detecting with high sensitivity the scattered light that has passed through the pinhole 734 in the pinhole plate 735.

The specularly reflected light detection optical system 740 includes: a mirror 741 for reflecting only specular light of all light reflected (specularly reflected light and scattered light) from the sample 1 and changing an optical path of the specularly reflected light; a converging lens 742 for converging the specularly reflected light changed in optical path by the mirror 741; and an imaging lens 743 for forming an image of the specularly reflected light on a second photoelectric converter 746 (e.g., APD), the specularly reflected light is converged by the converging lens 742 and passed through a pinhole 745 in a pinhole plate 744 by blocking stray light other than the specularly reflected light. The mirror 741 is formed into a shape small enough to prevent reflection of scattered light other than specular light. The second photoelectric converter 746 includes a plurality of detection elements, for example a plurality of photodiode arrays or avalanche photodiode (APD) arrays each having a plurality of pixels.

Figure 8A:
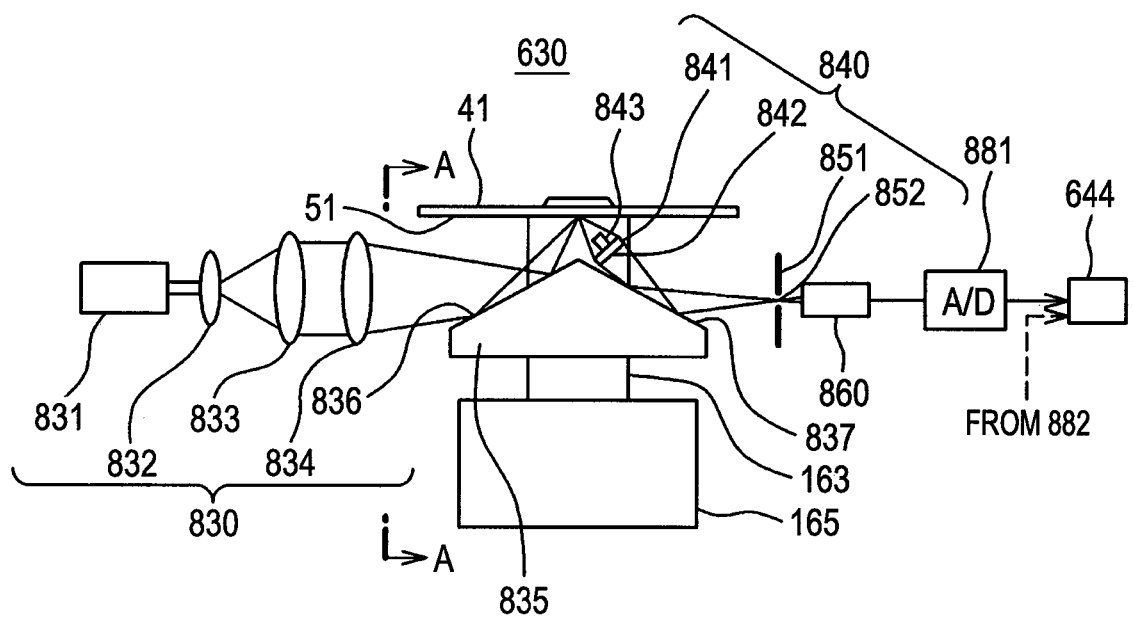
FIG. 8A is a front view showing a configuration of one of the optical systems for lower-surface inspection in the first embodiment.
Figure 8B:
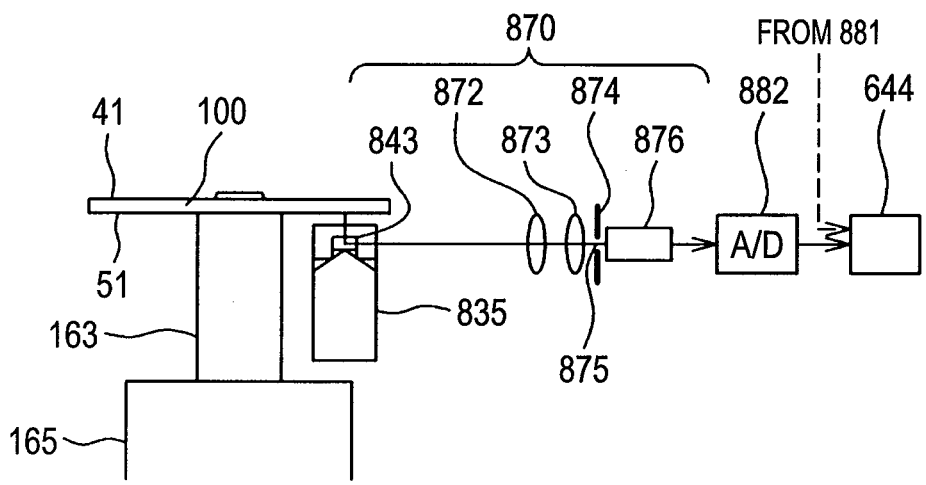
FIG. 8B is a side view of the other optical system for lower-surface inspection in the first embodiment.

A schematic configuration of the lower-surface inspection optical system 630 for detecting defects on the lower surface 51 of the sample 1 is shown in FIGS. 8A and 8B. The lower-surface inspection optical system 630 includes illumination optical system 830, scattered-light detection optical system 840, and specularly reflected light detection optical system 870.

As shown in FIG. 8A, the illumination optical system 830 of the lower-surface inspection optical system 630 includes: a second laser light source 831; a magnifying lens 832 for expanding a laser emitted from the second laser light source 831 in beam diameter; a converging lens 833 for converging the laser expanded in beam diameter by the magnifying lens 832; a focusing lens 834 for focusing the converged laser upon the lower surface 51 of the sample 1; and a prism 835 for changing an optical path of the laser passed through the converging lens 834. Since the prism 835 reflects the laser upon a facet 836 thereof and changes the optical path thereat, the second laser light source 831 can be disposed at a place distant from a relatively narrow space under a substrate 1. This layout enables the inspection of the lower surface without adding the table unit 610 any major changes or modifications, comparing to the conventional types of apparatuses inspecting one surface of a sample at a time.

Scattered-light detection optical system 840 for the lower surface includes: a third aspherical Fresnel lens 841 equivalent to an objective lens, for converging only scattered light of all light reflected (specularly reflected light and scattered light) from the lower surface 51 of the laser-irradiated sample 1; a fourth aspherical Fresnel lens 842 equivalent to a focusing lens, for focusing the scattered light that has been converged; a pinhole plate 851 having a pinhole 852 to let the scattered light pass through after changing in optical path by passing through the fourth aspherical Fresnel lens 842 and reflecting on a facet 837 of the prism 835, the pinhole plate 851 serving to block stray light other than the scattered light; and a third photoelectric converter 860, for example an avalanche photodiode (APD) or photomultiplier tube (PMT), for detecting with high sensitivity the scattered light that has passed through the pinhole 852 in the pinhole plate 851.

Because of the aspherical Fresnel lenses 841 and 842 being combined with the prism 835 in the scattered-light detection optical system 840 for the lower surface, optical system with a relatively large numerical aperture (NA) can be disposed in a relatively narrow space under the substrate 1. In addition to above, by introducing the prism 835 to change the optical path of the scattered light in direction enables the inspection of the lower surface without adding the table unit 610 any major changes or modifications, compared with those incorporated into conventional single-surface inspection apparatus.

As shown in FIG. 8B, specularly reflected light detection optical system 870 for the lower surface includes: a mirror 843 for reflecting only specular light of all light reflected (specularly reflected light and scattered light) from the lower surface 51 of the laser-irradiated sample 1 and changing an optical path of the specularly reflected light (in the configuration diagram of FIG. 8A, the mirror 843 reflecting scattered light in a direction perpendicular to the paper); a converging lens 872 for converging the specularly reflected light changed in optical path by the mirror 843; an imaging lens 873 for imaging the lower surface of the sample 1 by focusing the converged specularly reflected light; a pinhole plate 874 having a pinhole 875 to let the specularly reflected light pass through after being passed through the imaging lens 873, the pinhole plate 874 serving to block stray light other than the specularly reflected light from the lower surface of the sample 1; and a fourth photoelectric converter 876, for example an avalanche photodiode (APD), for detecting the image of the lower surface 51 of the sample that is formed by the imaging lens 873.

Operation of various constituent elements for inspecting the upper and lower surfaces of the magnetic disk at the same time in the above configurations is described below.

The spindle motor 163 is activated by a command from the signal-processing and total control unit 180 and rotates the sample 1 retained on the spindle shaft 161 by the chuck 162, and then the second motor 166 moves the moving stage 165 at a constant speed along the guide shaft 164. Under these conditions, the first laser light source 721 of the upper-surface inspection optical system 620 and the second laser light source 831 of the lower-surface inspection optical system 630, both optical systems 620 and 630 being controlled by the inspection optical system control unit 651, are activated to emit the respective laser beams.

First, defect inspection on the upper surface 41 of the sample 1 in the upper-surface inspection optical system 620 is described below by referring to FIG. 7.

A state of light reflected (scattered light and specularly reflected light) from the upper surface 41 of the laser-irradiated sample 1 depends on surface roughness due to presence of defects, flaws, microscopic projections/depressions, and/or the like. The scattered light from the sample 1 will be distributed according to particular dimensions of defects on the surface of the sample 1. That is, the light scattered from large defects or flaws, for example, will be distributed at a relatively high strength level and with directivity, whereas the light scattered from microscopic defects or flaws, for example, will be distributed in isotropic form at a relatively low strength level.

Specularly reflected light among the light reflected from the upper surface 41 of the laser-irradiated sample 1 travels in a direction of the converging lens 742 after being reflected by the mirror 741 disposed at the same exit angle (on the optical path of the specularly reflected light) as an angle of incidence of the laser incident upon the upper surface 41 of the sample 1. After the specularly reflected light from the sample 1 has entered the converging lens 742, the converging lens 742 transmits and converges the specularly reflected light, and then the imaging lens 743 forms an image of the upper surface 41 of the sample 1 on a light-receiving surface 747 of the second photoelectric converter 746 by passing the converged light through the pinhole 745 in the pinhole plate 744 disposed at the converging position. The mirror 741 has a small enough shape so that light (scattered light) other than the specularly reflected light is not reflected in the direction of the converging lens 742.

In contrast, of all light (scattered light) that has not been reflected by the mirror 741 after being reflected from the upper surface 41 of the laser-irradiated sample only light that has entered the first aspherical Fresnel lens 731 having a function of an objective lens is converged, then after entering the second aspherical Fresnel lens 732 having a function of a focusing lens, the particular light is focused on a detection surface (not shown) of the first photoelectric converter 736, and detected by this highly sensitive photoelectric converter.

The first aspherical Fresnel lens 731 and the second aspherical Fresnel lens 732 are thin and lightweight in comparison with conventional optical lenses. Barrels (not shown) for accommodating these lenses can therefore be made relatively compact relative to those of conventional optical lenses, which correspondingly increases flexibility of layout above the upper surface of the sample, enabling the layout to be designed with a numerical aperture (NA) of 0.6 or more (use of conventional optical lenses involves an NA of 0.4 or less). As a result, since the light scattered from microscopic defects will be distributed in substantially isotropic fashion over the substrate. In case the detection sensitivity is same, detection signal levels will be proportionate to an area of the detection surface. So, the detection signal levels obtained from the optical system 730 will be higher than those obtained during detection with any detection optical systems including conventional optical lenses. This means that the optical system 730 can detect the light scattered from defects smaller than those detectable with conventional optical system.

Analog/digital (A/D) converters 751 and 752 each convert the analog signal output from the first photoelectric converter 736 or the second photoelectric converter 746, into a digital signal, then amplify the digital signal, and output the amplified digital signal.

The digital signals that have been output from the A/D converters 751 and 752 are input to the signal-processing unit 643. The signal-processing unit 643 then uses both or one of the digitally converted original output signals from the first photoelectric converter 736 and second photoelectric converter 746 to process the input signals, detect defects present on the upper surface 41 of the sample 1, and identify positions of the detected defects on substrate 100 using the laser-irradiated position information on the sample 1, which is obtained from the total control unit 650 that controls the table 610. The signal-processing unit 643 additionally identifies the kinds of detected defects from features and characteristics of the detection signals output from the first photoelectric converter 736 and the second photoelectric converter 746. The results processed by the signal-processing unit 643 are sent to the integrated processing unit 645, wherein the processed results are then integrated with lower-surface inspection results. Integration results are next displayed on the display screen 648 of the input/output unit 647.

In the present embodiment, while a configuration including the first aspherical Fresnel lens 731 and the second aspherical Fresnel lens 732 in the scattered-light detection optical system 730 has been described, these lenses may be replaced by a combination of such aspherical lenses or normal spherical lenses.

Next, defect inspection on the lower surface 51 of the sample 1 in the lower-surface inspection optical system 120 is described below by referring to FIGS. 8A and 8B.

Laser that has been emitted from the second laser light source 831 is expanded in beam diameter by the magnifying lens 832, and then the laser that has been expanded in beam diameter is converged by the converging lens 833 to become parallel light and enter the focusing lens 834. The laser, after passing through the focusing lens 834, is reflected by the facet 836 of the prism 835, changed in optical path, and focused on the lower surface 51 of the sample 1 disposed on a focal position of the focusing lens 834.

The facet 836 of the prism 835 is preset for the reflected laser to enter the lower surface 51 of the sample 1 at a desired angle (about 30 degrees). Among the light reflected (specularly reflected light and scattered light) from the lower surface 51 of the sample 1 that has been irradiated with the focused laser beam, only the light directed towards the third aspherical Fresnel lens 841, which serves to converge light equivalently to an objective lens, enter the third aspherical Fresnel lens 841. The third aspherical Fresnel lens 841 is disposed so as to the focal position of it matches to a laser-irradiating position on the lower surface 51 of the sample 1. The light reflected from the lower surface 51 of the sample 1 and entered the third Fresnel lens 841 is converged thereat, and exit the third aspherical Fresnel lens 841 as parallel light. Meanwhile, specularly reflected light among the light reflected from the sample 1 directs towards the third aspherical Fresnel lens 841 and is reflected by the mirror 843 which is disposed in front of the Fresnel lens 841. The specularly reflected light reflected by the mirror 843 changes the optical path and does not enter the Fresnel lens 841.

The scattered light that has originated from the lower surface 51 of the sample 1 and has been admitted into and converged upon the third aspherical Fresnel lens 841 to become parallel light enters the fourth aspherical Fresnel lens 842 and passes through the Fresnel lens 842. Then, this light upon being reflected on the facet 837 of the prism 835 is changed in optical path and focused at a focal position of the fourth aspherical Fresnel lens 842. The facet 837 of the prism 835 is set to an angle so that the scattered light which is reflected from the facet 837 is directed in a desired direction (parallel to the lower surface 51 of the sample 1). In the present embodiment, in order that the laser from the second laser light source 831 travels in parallel to the lower surface of the sample 1 until the laser has reached the facet 836 of the prism 835. The facets 836 and 837 are set to have the same angle of inclination. The facets 836 and 837 of the prism 835 are both of mirror construction.

The pinhole plate 851, disposed at a focal position on the fourth aspherical Fresnel lens 842, is opened at the pinhole 852 to let the scattered light from the sample pass through upon being focused on the focal position. In contrast, a large portion of light other than the scattered light (i.e., reflected light from the prism 835 and other optical components: stray light) cannot pass through the pinhole 852 and is blocked by the pinhole plate 851, so a majority of the light detected by the third photoelectric converter 860 is the scattered light from the lower surface of the sample 1.

The signal output from the third photoelectric converter 860 by the detection of light scattered from the lower surface 51 of the sample 1 is input to an A/D converter 881 of the A/D conversion unit 641, and after being converted into digital signal form and amplified, this signal is input to the lower-surface detection signal-processing unit 644.

Meanwhile, as shown in FIG. 8B, the specularly reflected light from the sample 1 that has been reflected by the mirror 843, changed in optical path, and admitted into the lower-surface specularly reflected light detection optical system 870 for the lower surface, enters the converging lens 872, becomes converged by this lens, and further enters the imaging lens 873. The pinhole plate 874 with a pinhole 875 is disposed at the position where the specularly reflected light becomes converged after entering the imaging lens 873 and passing therethrough. The specularly reflected light that has passed through the imaging lens 873 has any stray light components to be removed during passage through the pinhole 875, then the light passed through the pinhole 875 forms an image of the lower surface 51 of the sample 1 on a detection surface of the fourth photoelectric converter 876, and is detected by the photoelectric converter 876. A detection signal output from the fourth photoelectric converter 876 by detecting the specularly reflected light is input to and amplified by an A/D converter 882 in the second A/D conversion unit 642, and this amplified signal is converted into a digital signal and then input to the lower-surface detection signal-processing unit 644.

The detection signal that has been sent as an input signal from the third photoelectric converter 860 to the lower-surface detection signal-processing unit 644, and the detection signal from the fourth photoelectric converter 876 undergo processing similar to the signals sent to the upper-surface detection signal-processing unit 643. Thus, corresponding defects on the lower surface 51 of the sample 1 are detected, the kinds and sizes of defects are identified, and identification results are sent with position information of the defects to the integrated processing unit 645.

According to the present embodiment, compact detection optical system with high NA can be constructed by combining aspherical Fresnel lenses, which in turn enables simultaneous detection of even more microscopic defects on both upper and lower surfaces of the substrate without upsizing the apparatus.

After data processing by the upper-surface detection signal-processing unit 643 and the lower-surface detection signal-processing unit 644, the data is sent to the integrated processing unit 645 and undergoes processing therein. This data is next sent to and stored into the storage unit 646 as double-surface defect information on the sample 1. The data is also sent to the input/output unit 647, at which unit inspection result information is then displayed on the screen 648.

Next, the read/write tests executed at the test position T are described by referring to FIGS. 9 to 11B.

During the read/write tests, both surfaces of the sample 1 are simultaneously inspected using the paired magnetic heads 131 and 132, as shown in FIG. 1. Since the paired magnetic heads 131 and 132 are of the same signal-processing circuit composition, the circuit composition of the magnetic head 131 is taken by way of example in the description per FIG. 9.

Figure 9:
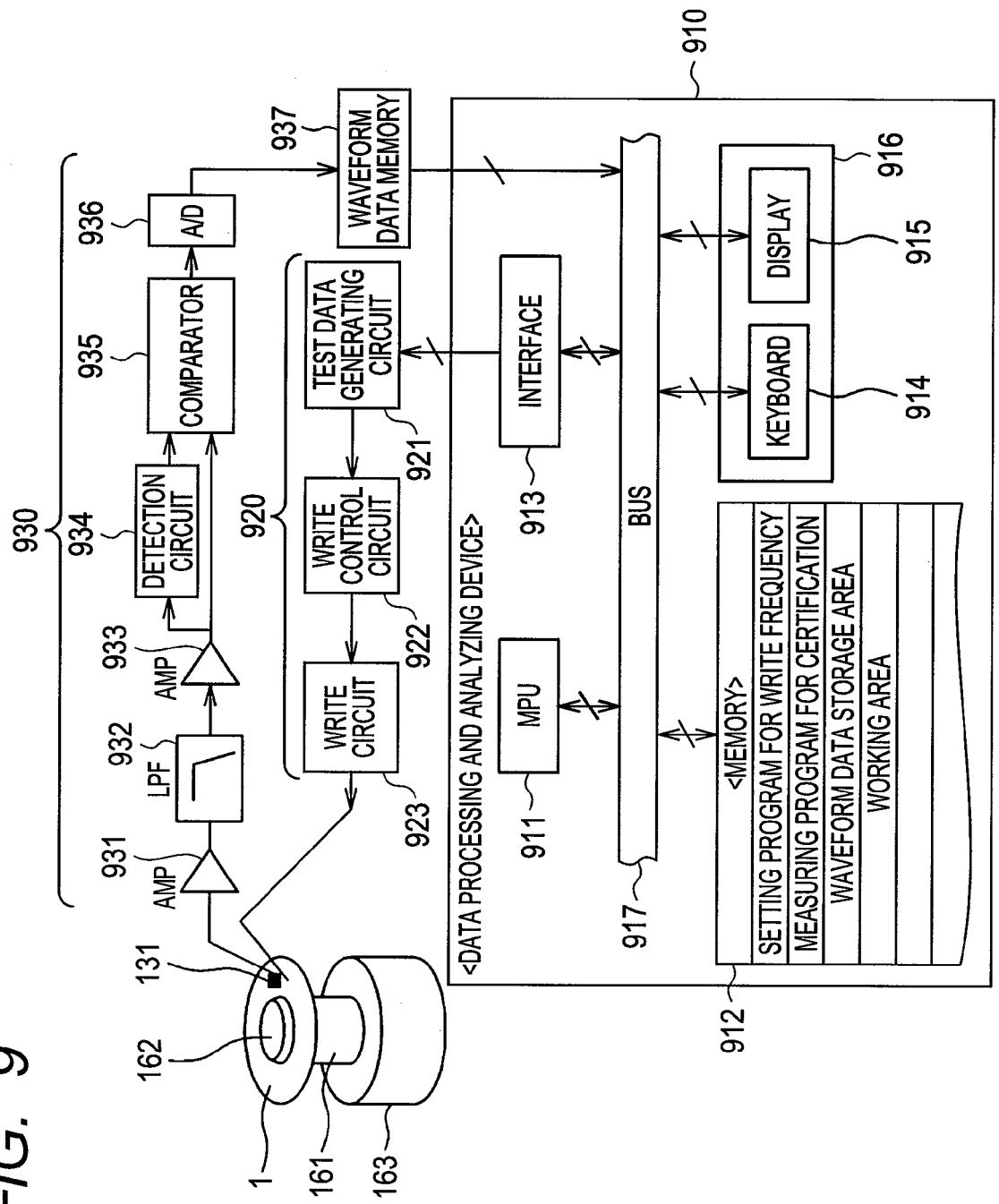
FIG. 9 is a block diagram showing a schematic configuration of a read/write test unit in the first embodiment.

The system configuration for conducting the read/write tests with the magnetic head 131 includes a data-processing and analyzing device 910, a writing circuit 920, and a readout circuit 930 as shown in FIG. 9. The data-processing and analyzing device 910 is included in the signal-processing and total control unit 180 of the inspection apparatus shown in FIG. 1.

The data-processing and analyzing device 910 includes an MPU 911 that directs and controls execution of a read/write test program and a data-processing program, a storage unit 912 for storing the read/write test program and data, an interface unit 913 that exchanges signals with the writing circuit 920, and an input/output unit 916 equipped with a keyboard 914 and a display 915. The MPU 911, the storage unit 912, the interface unit 913, and the input/output unit 916 also exchange signals with one another via a bus 917. The input/output unit 916 may be used as the input/output unit 647 of the optical inspection unit 100.

A setting program for write frequencies and a measuring program for certification are also stored in the storage unit 912. In addition, a storage area for waveform data is provided in the storage unit 912.

The writing circuit 920 includes: a test data generating circuit 921 that generates test data based on the write frequency data output from the data-processing and analyzing device 910 via the interface 913, and on the position data relating to the defects detected by the optical inspection unit 100 (i.e., radial (R)-coordinate data in the areas where the defects on the sample 1 exist); a write control circuit 922 that controls writing of the generated test data onto the sample 1; and a write circuit 923 controlled by the write control circuit 922 to apply the test data to the magnetic head 131 and write data onto predetermined tracks on the sample 1 (i.e., the tracks where the defects detected by the optical inspection unit 100 are present).

The readout circuit 930 includes: a first amplifier 931 for amplifying a signal that the magnetic head 131 outputs upon detecting the data written onto the sample 1; a low-pass filter 932 for reducing a noise signal level of high-frequency components with respect to the output signal from the first amplifier 931; a second amplifier 933 for further amplifying a signal output from the low-pass filter 932; a track average amplitude (TAA) detection circuit 934 for obtaining an average voltage level of a track readout waveform from a signal output from the second amplifier 933; a comparator 935 for comparing the average voltage level of the track readout waveform obtained in the TAA detection circuit 934 and the output signal from the second amplifier 933; an A/D converter 936 for binarizing a signal output from the comparator 935; and a waveform data memory 937 for storing a waveform of a signal output from the A/D converter 936.

Figure 5:
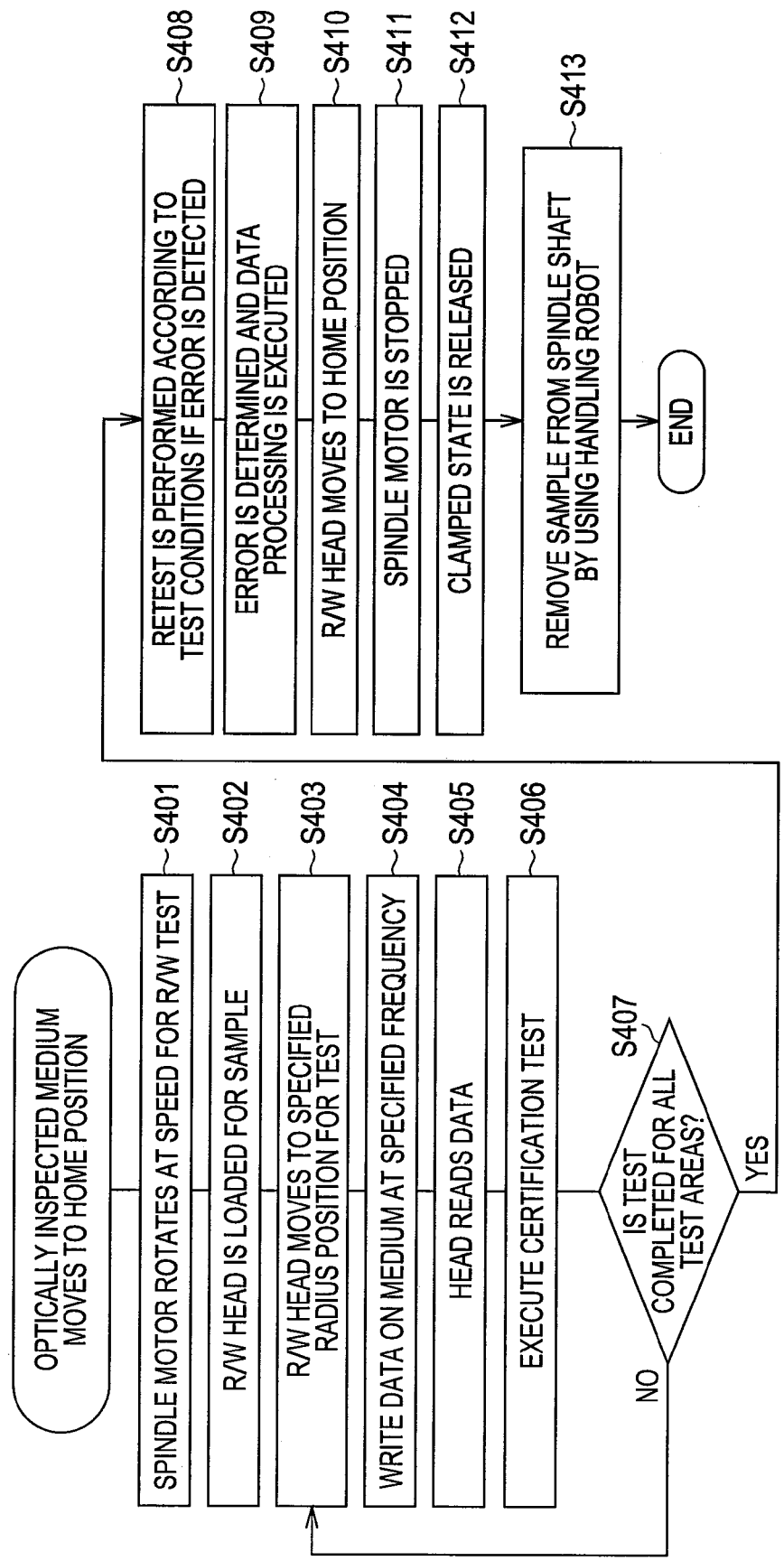
FIG. 5 is a flow diagram for describing read/write test process steps according to the first embodiment.

The read/write test unit 130 of the above configuration is used to conduct read/write tests in the sequence as described in FIG. 5.

Figure 10B:
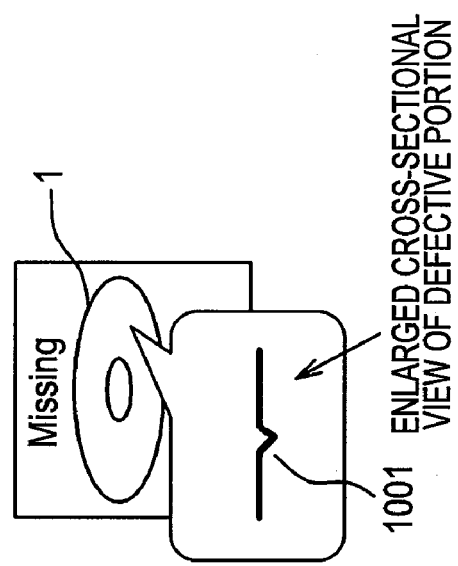
FIGS. 10A and 10B relate to detection of a concave-like defect during read/write tests in the first embodiment.
Figure 10A:
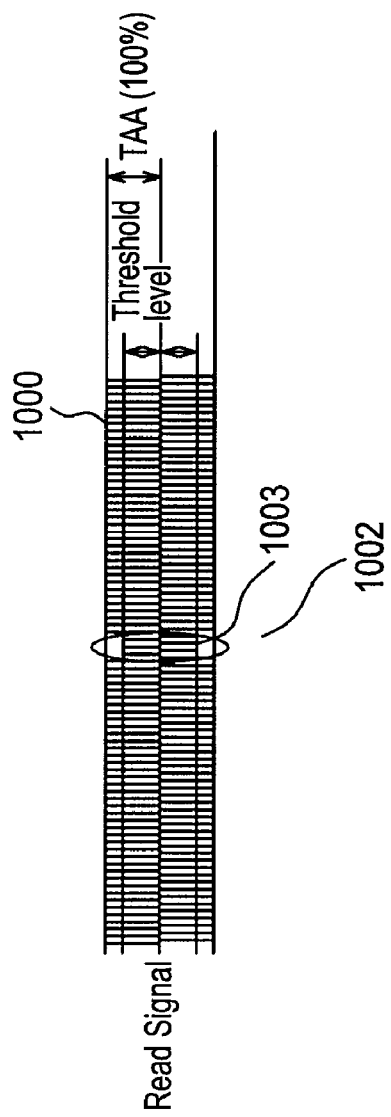

FIGS. 10A and 10B show an example of a signal output from the comparator 935 during read/write testing of an area on the sample 1 where a concave defect exists.

After input of the radial position information relating to a defect detected on the sample 1 by the optical inspection unit 100, when a read/write test is conducted upon an upper-surface area having, on the sample 1, such a concave defect as shown in FIG. 10B, the concave defective portion 1001, compared with a nondefective portion, is extended in terms of a clearance between the magnetic head 131 flying above the upper surface of the sample 1 rotating at high speed, and the sample's surface section currently undergoing the data read/write process. Therefore, a level of a signal written by the magnetic head 131 after receiving a corresponding signal from the writing circuit 920 decreases below a signal level corresponding to the nondefective portion. Additionally, when the data that has been written onto the sample 1 is read out by the readout circuit 930, the clearance at the concave defective portion with respect to the magnetic head 131 is extended in comparison with that of the nondefective portion. Therefore, the detection signal level correspondingly decreases. As a result, as shown in FIG. 10A, the detection signal takes a waveform 1000 indicating that a crest value 1003 of the concave defective portion enclosed in an ellipse 1002 is smaller than those of other portions, and hence that a readout error is occurring at the concave defective portion.

Figure 11A:
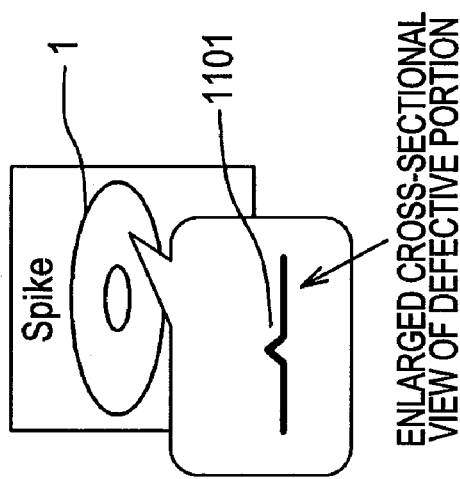
FIGS. 11A and 11B relate to detection of a convex-like defect during read/write tests in the first embodiment.
Figure 11B:
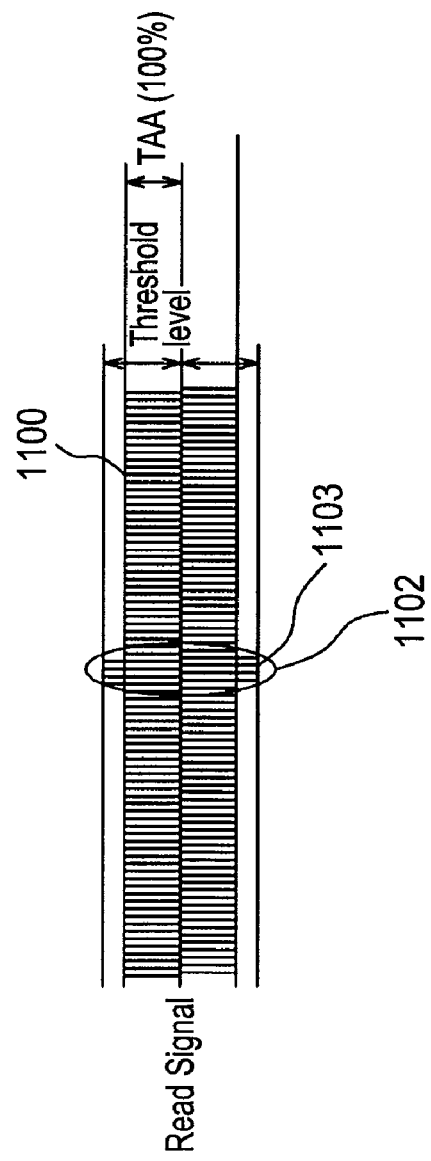

Conversely, such a convex defective portion 1101 as shown in FIG. 11B decreases in terms of a clearance with respect to the magnetic head 131 compared with a nondefective portion, so a level of a signal written by the magnetic head 131 after receiving a corresponding signal from the writing circuit 920 increases above a signal level of the nondefective portion. Additionally, when data that has been written onto the sample 1 is read out by the readout circuit 930, the clearance at the convex defective portion with respect to the magnetic head 131 decreases in comparison with that of the nondefective portion, so that the detection signal level correspondingly increases. As a result, as shown in FIG. 11A, the detection signal takes a waveform 1100 indicating that a crest value 1103 of the convex defective portion enclosed in an ellipse 1102 is greater than those of other portions, and hence that a readout error is occurring at the convex defective portion.

Although the read/write test unit 1301 in the system configuration of FIG. 1 uses the paired magnetic heads 131 and 132 to simultaneously inspect both surfaces of the sample 1, the present invention is not limited to or by this form of magnetic head arrangement. Two pairs or more pairs of magnetic heads may be combined for double-surface simultaneous read/write testing on multiple sections of the sample.

According to the present embodiment, since read/write tests can be performed without removing the sample from the spindle on which the sample has been set for optical inspection, position data on the defects detected during optical inspection can be used for the read/write tests. This enables reliable and efficient read/write testing of the area including the detected defects.

Second Embodiment

In the system configuration of the first embodiment described in FIG. 1, while the optical inspection unit 100 is executing optical inspection, the sample 1 is absent in the read/write test unit 130 and this test unit is waiting for the optical inspection in the optical inspection unit 100 to come to an end. Conversely, while the read/write test unit 130 is executing read/write tests of the sample 1, the optical inspection unit 100 is waiting for the tests to end. In the inspection apparatus configuration described in the first embodiment, therefore, inspection throughput is likely to decrease to half as much as it is achievable if the optical inspection unit 100 and the read/write test unit 130 are each constructed independently.

Accordingly, a second embodiment employs a configuration that enables a sample to be tested by moving it from an optical inspection unit to a read/write test unit without reducing throughput and without removing the sample from a spindle.

The second embodiment based on the above standpoint is described below using FIG. 12.

Figure 12:
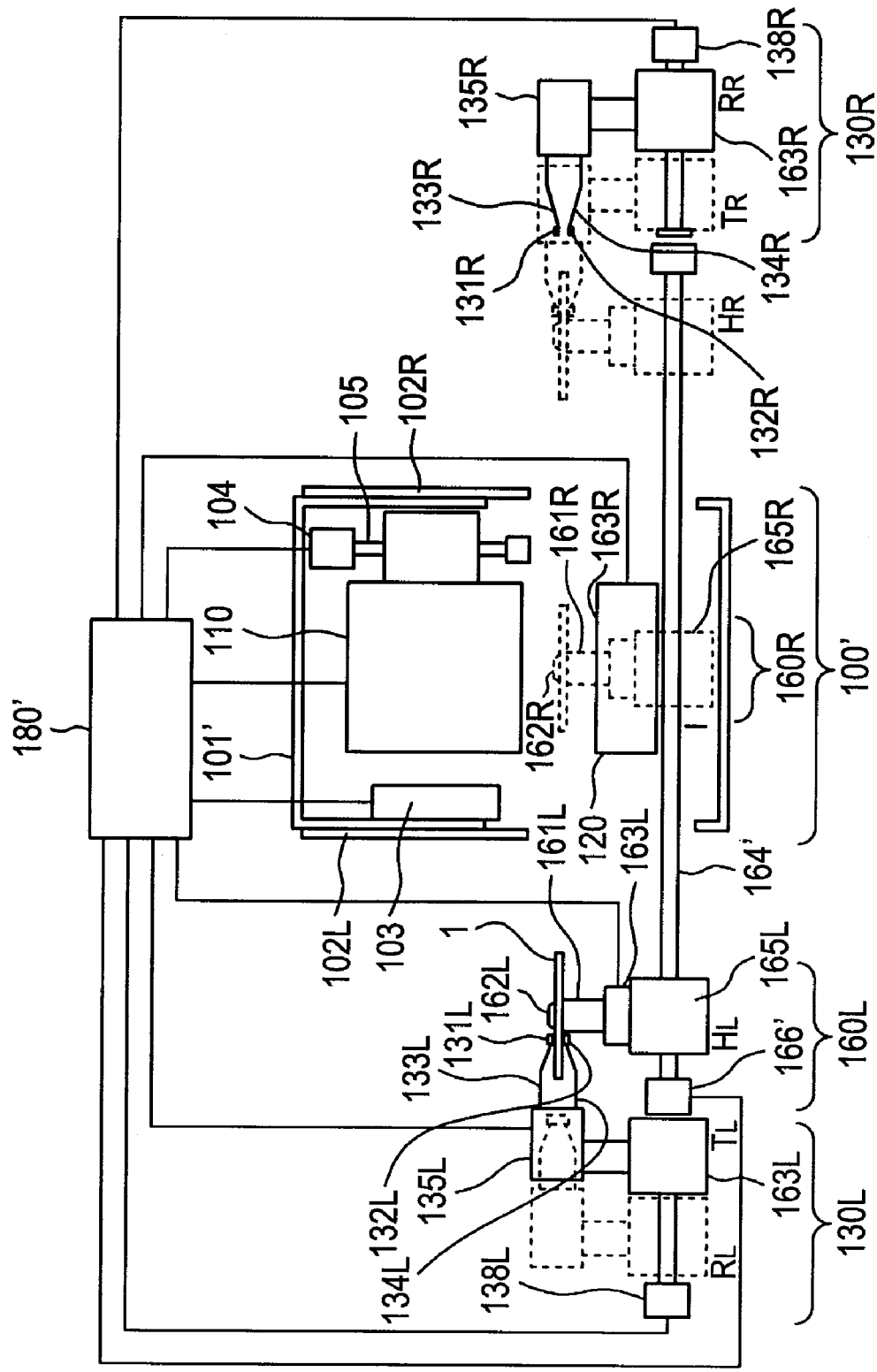
FIG. 12 is a block diagram showing a total system configuration of an inspection apparatus according to a second embodiment.
Figure 13:
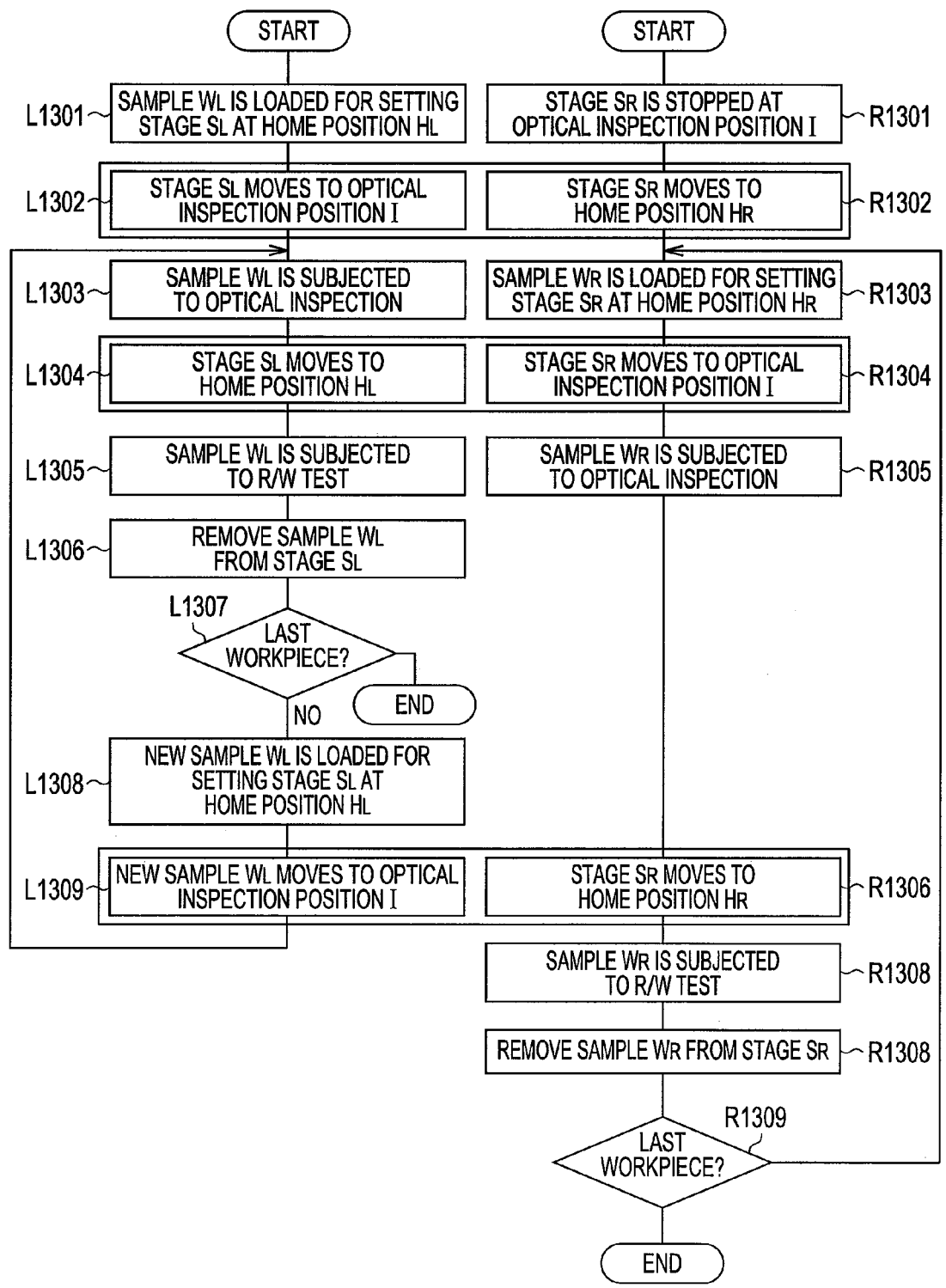
FIG. 13 is a flow diagram showing a flow of processing in the inspection apparatus according to the second embodiment.

The system configuration of the second embodiment shown in FIG. 12 differs from the first embodiment of FIG. 1 in that the apparatus includes read/write test units 130L and 130R across the optical inspection unit 100', and in that two sample transport units, 160L and 160R, are further added.

Configurations of the read/write test unit 130L and sample transport units 160L and 160R are the same as those described in the first embodiment, and the read/write test unit 130R takes a configuration that is left/right symmetrical to that of the read/write test unit 130L.

In addition, the optical inspection unit 100' has shutters 102L and 102R arranged to the left and right, respectively, of its protective cover 101'.

Furthermore, the sample transport unit 160 has a guide shaft 164' ranging in length from a home position HL of a moving stage 165L to a home position HR of a moving stage 165R, and the moving stages 165L and 165R are both driven by a second motor 166'. The moving stage 165L at left and the moving stage 165R at right are each connected to the guide shaft 164' at a fixed interval.

Constituent elements of each unit are the same as those described in the first embodiment. Description of these elements is therefore omitted.

The following sets forth optical inspection and read/write test execution sequences based on the above system configuration.

First, when the left moving stage 165L is present at the home position HL and the right moving stage 165R at an optical inspection position I, a new sample L1 at the home position HL is supplied to a spindle shaft 161L and then clamped with a chuck 162L (step L1301). During this time, the right moving stage 165R remains stopped at the optical inspection position I (step R1301).

At the home position HL, upon the new sample L1 being clamped by the chuck, the left moving stage 165L and the right moving stage 165R are both driven by the second motor 166' and start moving to the right of FIG. 12 along the guide shaft 164' (steps L1302, R1302). More specifically, the left moving stage 165L moves to the inspection position I at the optical inspection unit 100', and the right moving stage 165R moves to the right home position HR.

Under this state, the sample L1 clamped by the chuck 162L on the spindle shaft 161L of the left moving stage 165L is inspected by the optical inspection unit 100' in a manner similar to that of the optical inspection in the first embodiment (step L1303). At the home position HR, in contrast, a sample R1 is supplied to a spindle shaft 161R by a handling robot (not shown), and then clamped by a chuck 162R (step S1303).

Upon completion of both the optical inspection of the sample L1 and the chuck clamping of the sample R1, the left moving stage 165L and the right moving stage 165R are both driven by the second motor 166' and start moving to the left of FIG. 12 along the guide shaft 164' (steps L1304, R1304). More specifically, the left moving stage 165L moves to the left home position HL, and the right moving stage 165R moves to the inspection position I at the optical inspection unit 100'.

Under this state, the left moving stage 165L is driven by a spindle motor 163L to rotate the sample L1. Read/write testing of the rotating sample L1, based on the defect candidate position information previously obtained during the inspection with the optical inspection unit 100', is then executed using one pair of magnetic heads 131L and 132L whose radial positions above and below the sample L1 are controlled by driving with a first motor 138L (step L1305). The test sequence is substantially the same as that described in the first embodiment.

Upon completion of the sample-L1 read/write tests at the left home position HL, the chuck 162L unclamps the sample L1 and the handling robot (not shown) removes the sample L1 from the spindle shaft 161L (step L1306). Whether a next sample to be inspected is present is determined (step L1307) and if a new sample L2 to be inspected is present, the new sample L2 is supplied to the spindle shaft 161L and clamped by the chuck 162L (step L1308).

Inspection at the spindle 161L ends if the sample L2 to be next inspected is absent.

Meanwhile, the sample R1 clamped by the chuck 162R on the spindle shaft 161R of the right moving stage 165R is optically inspected at the optical inspection unit 100' in substantially the same sequence as that described in the first embodiment (step R1305).

When the optical inspection of the sample R1 at the optical inspection unit 100' ends and supply of the new sample L2 to the spindle shaft 161L at the home position HL is completed, the left moving stage 165L and the right moving stage 165R are driven by the second motor 166' and start moving to the right of FIG. 12 along the guide shaft 164' (steps L1309, R1306). More specifically, the left moving stage 165L moves to the inspection position I at the optical inspection unit 100', and the right moving stage 165R moves to the right home position HR.

Under this state, the right moving stage 165R is driven by a spindle motor 163R to rotate the sample R1. Read/write testing of the rotating sample R1, based on the defect candidate position information previously obtained during the inspection with the optical inspection unit 100', is then executed using one pair of magnetic heads 131R and 132R whose radial positions above and below the sample R1 are controlled by driving with a third motor 138R (step R1307). The test sequence is substantially the same as that described in the first embodiment.

Upon completion of the sample-R1 read/write tests at the right home position HR, the chuck 162R unclamps the sample R1 and the handling robot (not shown) removes the sample R1 from the spindle shaft 161R (step R1308). Whether a next sample to be inspected is present is determined (step R1309) and if a new sample R2 to be inspected is present, test control is returned to step R1303, in which the new sample R2 is then supplied to the spindle shaft 161R by the handling robot and clamped by the chuck 162R.

Inspection at the spindle 161R ends if the sample R2 to be next inspected is absent.

Meanwhile, if the left moving stage 165L is already set to the inspection position I at the optical inspection unit 100' with a new sample L2 supplied to the spindle shaft 161L and clamped by the chuck 162L, test control is returned to step L1303 and optical inspection is executed.

According to the present embodiment, the loading/unloading and read/write testing of samples alternates between the left home position HL and the right home position HR. Samples can therefore be continuously processed without generating a process waiting time at the read/write test units 130L and 130R or the optical inspection unit 100'.

The invention may be embodied in other specific forms without departing from the spirit or essential characteristics thereof. The present embodiment is therefore to be considered in all respects as illustrative and not restrictive, the scope of the invention being indicated by the appended claims, rather than by the foregoing description, and all changes which come within the meaning and range of equivalency of the claims are therefore intended to be embraced therein.

The invention claimed is:

1. An apparatus for inspecting defects on a surface of a magnetic disk which is a sample, the apparatus comprising:
    optical inspection means for optically inspecting the surface of the sample and detecting defects on the surface of the sample;
    read/write test means for determining a state of the sample by conducting read/write tests during which the read/write test means itself uses magnetic heads to write information onto the sample inspected by the optical inspection means and read the written information from the sample; and
    spindle shaft means for rotating the sample rested and retained thereupon, the spindle shaft means, upon completion of the inspection by the optical inspection means, moving the rested sample to the read/write test means for execution of the read/write tests.

2. The magnetic disk inspection apparatus according to claim 1, wherein, on the basis of position information relating to the defects detected during the inspection by the optical inspection means, the read/write test means selectively conducts the read/write tests upon corresponding positions of the defects detected by the optical inspection means.

3. The magnetic disk inspection apparatus according to claim 1, wherein the read/write test means includes one pair of magnetic heads, the read/write test means moving the paired magnetic heads to access a surface of one side of the sample and an another surface of the other side of the sample and conduct the read/write tests upon the lower and upper surfaces of the sample at the same time.

4. The magnetic disk inspection apparatus according to claim 1, wherein the optical inspection means includes an optical system for optically inspecting a surface of one side of the sample, and an optical system for optically inspecting an another surface of the other side of the sample, the one side surface inspection optical system and the other side surface inspection optical system optically inspecting the surfaces of both sides of the sample at the same time.

5. An apparatus for inspecting defects on surfaces of both sides of a magnetic disk which is a sample, the apparatus comprising:
    double-surface simultaneous optical inspection unit which optically inspects surfaces of both sides of the sample at the same time and detecting defects on the surfaces of both sides of the sample;
    read/write test unit which determines a state of defects detected by the optical inspection means, by conducting read/write tests during which the read/write test means itself uses magnetic heads to write information onto positions inclusive of the detected defects on the surfaces of both sides of the sample, and read the written information from the sample; and
    spindle shaft unit which is constructed to move, with the sample rested and retained thereon, between the double-surface simultaneous optical inspection means and the read/write test means, the spindle shaft unit rotationally driving the rested sample at a position of the double-surface simultaneous optical inspection means and that of the read/write test means.

6. The magnetic disk inspection apparatus according to claim 5, wherein the double-surface simultaneous optical inspection means uses a Fresnel lens as an objective lens.

7. The magnetic disk inspection apparatus according to claim 5, wherein, on the basis of position information relating to the defects detected on the surfaces of both sides of the sample by the double-surface simultaneous optical inspection means, the read/write test means determines positions on the sample where the read/write tests are to be conducted.

8. The magnetic disk inspection apparatus according to claim 5, wherein the read/write test means are installed on both sides of the double-surface simultaneous optical inspection means, the read/write test means on both sides of the double-surface simultaneous optical inspection means alternately conduct read/write tests upon the sample optically inspected in order by the double-surface simultaneous optical inspection means.

9. A method for inspecting a magnetic disk, the method comprising:
    optically inspecting surfaces of both sides of the magnetic disk at the same time and detecting defects on the surfaces of both sides of the sample; and
    conducting read/write tests to write information onto positions inclusive of any defects detected on either of the surfaces of both sides of the sample by the optical inspecting and read the written information to determine a state of the detected defects on the sample;
    wherein in the optically inspecting step, the surfaces of both sides of the sample are inspected at the same time while the sample is in a rested and retained condition on a spindle shaft which is constructed to rotationally drive the sample rested and retained thereon.

10. The magnetic disk inspection method according to claim 9, wherein in the step of optically inspecting, detecting defects on surfaces of both sides of the sample by processing signals output from a detector which detects light from the sample through a Fresnel lens.

11. The magnetic disk inspection method according to claim 9, wherein positions on the sample where the read/write tests are to be conducted are determined using position information relating to the defects detected on the surface of either sides of the sample by the optical inspection.

12. The magnetic disk inspection method according to claim 9, wherein a pair of read/write test means which conduct the read/write test are provided on both sides of a double-surface simultaneous optical inspection means which conducts the optical inspection and said pair of read/write test means alternatively conduct read/write tests upon the sample optically inspected in order by the double-surface simultaneous optical inspection means.

13. A method for inspecting a magnetic disk, the method comprising:

optically inspecting surfaces of both sides of the magnetic disk retained as a sample on a rotatably constructed spindle shaft at the same time, and detecting defects on the surfaces of both sides of the sample;

moving the sample from the optical inspection station to a read/write test station with the sample remaining retained on the spindle shaft; and conducting read/write tests by using magnetic heads to write information onto positions inclusive of the defects detected on either of the surfaces of both sides of the sample detected by the optical inspection and read the written information, whereby a state of the detected defects on the sample is determined by the read/write test.

14. The magnetic disk inspection method according to claim 13, wherein in the step of optically inspecting, detecting defects on the surfaces of both sides of the sample by processing signals output from a detector which detects light from the sample through a Fresnel lens.

15. The magnetic disk inspection method according to claim 13, wherein positions on the sample where the read/write tests are to be conducted are determined using position information relating to the defects detected on either of the surfaces of both sides of the sample during the optical inspection.

16. The magnetic disk inspection method according to claim 13, wherein the optically inspected samples are alternatively moved to different read/write stations to conduct the read/write test.

* * * * *